US011224380B2

(12) United States Patent
Alnofeli et al.

(10) Patent No.: US 11,224,380 B2
(45) Date of Patent: Jan. 18, 2022

(54) ANIMAL HEALTH SYSTEM AND METHOD FOR MONITORING PERFORMANCE

(71) Applicant: Khalifa University of Science and Technology, Abu Dhabi (AE)

(72) Inventors: Saeed Alnofeli, Abu Dhabi (AE); David Khayati, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 276 days.

(21) Appl. No.: 16/470,093

(22) PCT Filed: Dec. 20, 2017

(86) PCT No.: PCT/IB2017/058233
§ 371 (c)(1),
(2) Date: Jun. 14, 2019

(87) PCT Pub. No.: WO2018/116221
PCT Pub. Date: Jun. 28, 2018

(65) Prior Publication Data
US 2020/0015740 A1    Jan. 16, 2020

Related U.S. Application Data

(60) Provisional application No. 62/437,255, filed on Dec. 21, 2016.

(51) Int. Cl.
*A61B 5/00* (2006.01)
*A01K 11/00* (2006.01)
(Continued)

(52) U.S. Cl.
CPC .......... *A61B 5/4845* (2013.01); *A01K 11/008* (2013.01); *A01K 29/005* (2013.01);
(Continued)

(58) Field of Classification Search
CPC . A61B 5/4845; A61B 5/0205; A61B 5/02055; A61B 5/024; A61B 2503/40;
(Continued)

(56) References Cited

U.S. PATENT DOCUMENTS

2016/0367188 A1* 12/2016 Malik ................... G16H 40/67
2017/0095206 A1* 4/2017 Leib ..................... A01K 11/008

* cited by examiner

*Primary Examiner* — Hongmin Fan
(74) *Attorney, Agent, or Firm* — Billion & Armitage

(57) ABSTRACT

Systems and methods for monitoring an animal include receiving a plurality of biological parameters of the animal from a plurality of biological sensors, receiving location parameters of the animal from at least one location sensor, receiving weather parameters corresponding to ambient weather conditions proximate the animal from at least one ambient weather sensor, and comparing at least one of the parameters generated by the sensors with data representing at least one signature corresponding to the animal to determine if there is an irregular parameter. In response to an irregular reading/parameter being identified, then determining if the identified irregular parameter is related to a health condition of the animal and if the identified irregular parameter is not related to the health condition of the animal, then determining if the identified irregular parameter is related to an illegal activity.

18 Claims, 12 Drawing Sheets

(51) Int. Cl.
  *A61B 5/0205*    (2006.01)
  *A61N 1/18*      (2006.01)
  *A01K 29/00*     (2006.01)
  A61B 5/021       (2006.01)
  A61B 5/024       (2006.01)
  A61B 5/08        (2006.01)
(52) U.S. Cl.
  CPC ........ *A61B 5/0205* (2013.01); *A61B 5/02055* (2013.01); *A61B 5/4872* (2013.01); *A61B 5/4875* (2013.01); *A61N 1/18* (2013.01); *A61B 5/021* (2013.01); *A61B 5/024* (2013.01); *A61B 5/0816* (2013.01); *A61B 2503/40* (2013.01); *A61B 2560/0252* (2013.01)
(58) Field of Classification Search
  CPC .......... A61B 2560/0252; A61B 5/0024; A61B 5/112; A01K 29/005; A01K 11/008
  See application file for complete search history.

(1st beat) right hind leg
(2nd beat) right fore leg
(3rd beat) left hind leg
(4th beat) left fore leg Walk (1st beat) right fore / left hind
(2nd beat) left fore / right hind Trot (a)

(b)

The Right-Lead Canter:

(1st beat) left hind leg
(2nd beat) right hind / left fore
(3rd beat) right fore leg The Left-Lead Canter:

(1st beat) right hind leg
(2nd beat) left hind / right fore
(3rd beat) left fore leg Canter (c)

The Right-Lead Gallop:

(1st beat) left hind leg
(2nd beat) right hind leg
(3rd beat) left fore leg
(4th beat) right fore leg The Left-Lead Gallop:

(1st beat) right hind leg
(2nd beat) left hind leg
(3rd beat) right fore leg
(4th beat) left fore leg Gallop (d)

FIG. 5

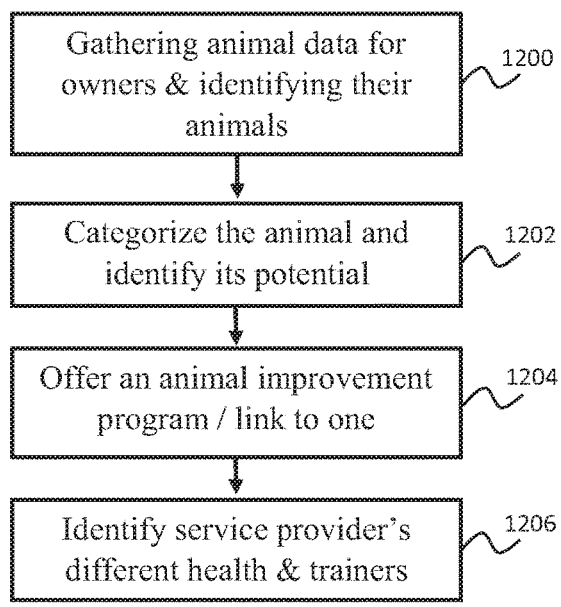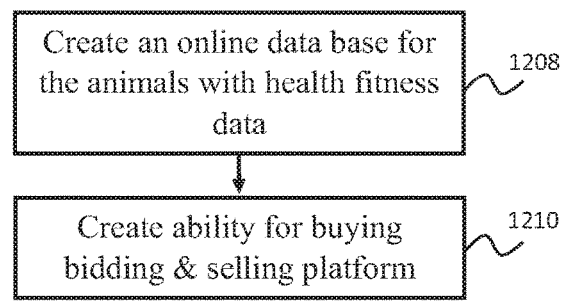
FIG. 12A
FIG. 12B

ANIMAL HEALTH SYSTEM AND METHOD FOR MONITORING PERFORMANCE

CROSS-REFERENCE TO RELATED APPLICATION

This application claims the benefit of U.S. provisional patent application Ser. No. 62/437,255, filed Dec. 21, 2016, the entire disclosure of which is incorporated herein by reference.

TECHNICAL FIELD

This disclosure relates to systems and methods including electronic feedback and communication for tracking, diagnosing, improving, and/or protecting the health and/or performance of an animal.

BACKGROUND

The "BACKGROUND" description provided herein is for the purpose of generally presenting the context of the disclosure. Work of the presently named inventor, to the extent it is described in this background section, as well as aspects of the description which may not otherwise qualify as prior art at the time of filing, are neither expressly nor impliedly admitted as prior art against the present disclosure.

Tracking physical attributes of people and animals has become a growing interest amongst fitness enthusiasts and trainers. Subsequently, a strong market is developing for technologies relating to tracking the heart rate, blood pressure, calories burnt, etc.

The information from the technology is very useful to track how a person or animal's health is at a certain time or date to where it has progressed after a period of time. Using such information from tracking technology enables users to understand the outcomes of their fitness strategies and to coordinate their routines better.

Collecting data on a person or animal and storing it in a database enables the ability to create applications that not only monitor but generate useful advice on how their health and fitness can be improved.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5(*a*) shows walk gait steps of an animal;
FIG. 5(*b*) shows trot gait steps of an animal;
FIG. 5(*c*) shows canter gait steps of an animal;
FIG. 5(*d*) shows gallop gait steps of an animal;

FIG. 12A indicates ways that the system can be used to create a valuable service to users, such as animal trainers and athletes; and FIG. 12B indicates other ways that the system can be used to create a valuable service to users, such as animal trainers and athletes.

DETAILED DESCRIPTION

Figure 1:
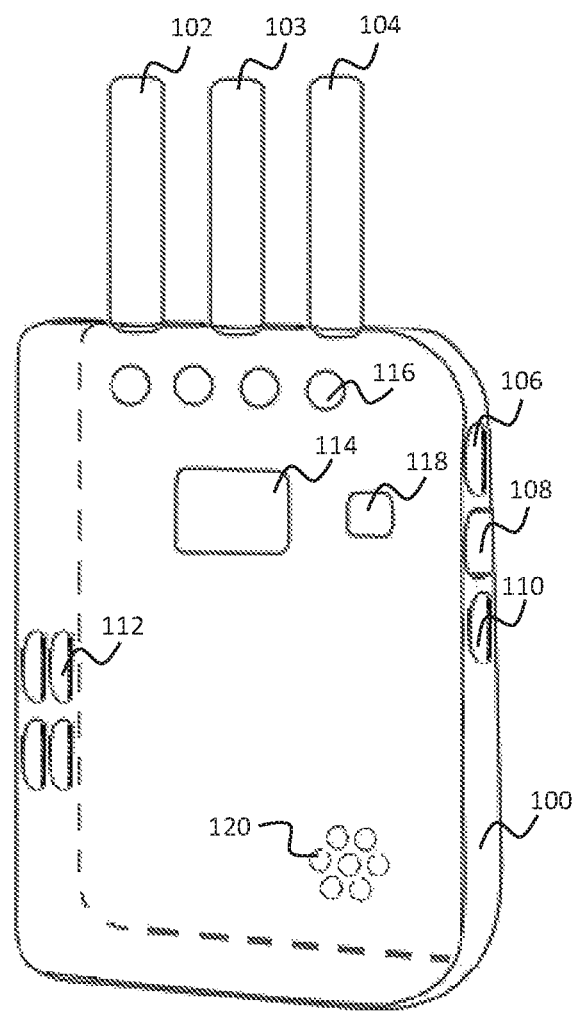
FIG. 1 is an exemplary illustration of the monitoring apparatus.

Referring now to the drawings, wherein like reference numerals designate identical or corresponding parts throughout the several views, FIG. 1 illustrates an exemplary animal monitoring device 100 upon which an embodiment of the present disclosure may be implemented. The monitoring device 100 embodies a number of components that work together to track and obtain different characteristics of an animal. The monitoring apparatus 100 communicates wirelessly to external communication networks using wireless communication components such as a wireless GSM/GPS antenna 102 for transmitting and receiving information to and from the apparatus, a wifi antenna for digital data transmission 103 as well as and a UHF/VHF frequency communication antenna 104 for wireless communication of the monitoring device. Also incorporated in the monitoring device 100 is a wireless personal area network antenna for sending and receiving information, with all the antennas combined the wireless transmissions cover Personal Area Network PAN, Local Area Network LAN and Wide Area Network WAN. Other data transfer methods for the monitoring device 100 include a USB connection 106 for direct data transfer to and from the monitoring device 100, an Ethernet connection 108, a micro USB 110 and a serial port 112. The connections allow digital interface between the monitoring device 100 and outside data sources through an integrated communication interface within the monitoring device 100. These connections enable the monitoring device 100 to connect to other apparatuses such as external video cameras, loud speakers, microphones, other sensory equipment, etc, for example, as described herein.

The monitoring device 100 contains an exemplary power switch 118 which controls the power activation within the monitoring device 100. When switched in an 'on' state, the monitoring device 100 is activated from an 'off' state and operates its programmed functions. The power switch 118 may take the form of a push button, a touch activation or remote operation. The function on of component 118 is to simply activate the monitoring device 100 from an 'off' state to an 'on' state. The monitoring device 100 also includes a visual display 114 to aid the user to understand the interaction being made with the monitoring device 100. In addition to the visual display 114, a number of optional LED indicators 116 may also be integrated to aid user with informing them of the activated functions of the monitoring device 100. In addition to visual displays on the monitoring device 100, the monitoring device 100 may optionally include one or more loud speakers 120 to either send messages to the user or to the animal it is attached to.

Figure 2:
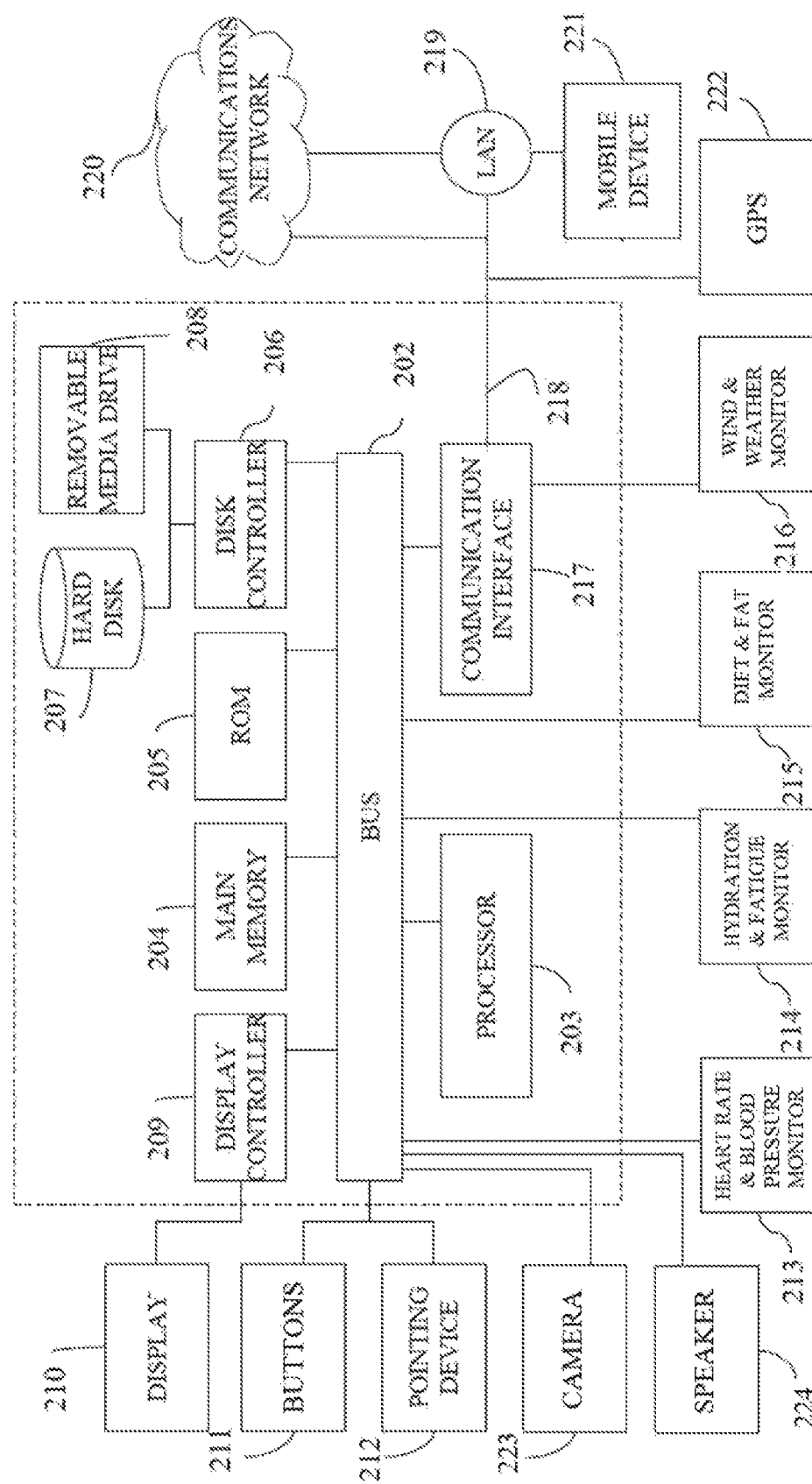
FIG. 2 is an exemplary is an exemplary block diagram of a hardware implementation, according to certain embodiments.

Referring to FIG. 2, the animal monitoring device 100 includes a bus 202 or other communication mechanism for communicating information, and a processor 203 coupled with the bus 202 for processing the information. The animal monitoring device 100 also includes a main memory 204 (such as a random access memory (RAM) or other dynamic storage device including, e.g., dynamic RAM (DRAM), static RAM (SRAM), and synchronous DRAM (SDRAM)) coupled to the bus 202 for storing information and instructions to be executed by processor 203. In addition, the main memory 204 may be used for storing temporary variables or other intermediate information during the execution of instructions by the processor 203. The animal monitoring device 100 further includes a read only memory (ROM) 205 or other static storage device (e.g., programmable ROM (PROM), erasable PROM (EPROM), and electrically erasable PROM (EEPROM)) coupled to the bus 202 for storing static information and instructions for the processor 203.

The animal monitoring device 100 also includes a disk controller 206 coupled to the bus 202 to control one or more storage devices for storing information and instructions, such as a magnetic hard disk 207, and a removable media drive 208 (e.g., floppy disk drive, read-only compact disc drive, read/write compact disc drive, compact disc jukebox, tape drive, and removable magneto-optical drive). The storage devices may be added to the animal monitoring device 100 using an appropriate device interface (e.g., small computer system interface (SCSI), integrated device electronics (IDE), enhanced-IDE (E-IDE), direct memory access (DMA), or ultra-DMA).

The animal monitoring device 100 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The animal monitoring device 100 may also include a display controller 209 coupled to the bus 202 to control a display 210, such as a liquid crystal display (LCD), for displaying information to a computer user. The animal monitoring device 100 includes input devices, such as input touch buttons 211 and a pointing device 212, for interacting with a user and providing information to the processor 203. The pointing device 212, for example, may be a mouse, a trackball, or a pointing stick for communicating direction information and command selections to the processor 203 and for controlling cursor movement on the display 210. In addition, a printer (not shown) may provide printed listings of data stored and/or generated by the computer system 201.

The animal monitoring device 100 performs a portion or all of the processing steps of the present disclosure in response to the processor 203 executing one or more sequences of one or more instructions contained in a memory, such as the main memory 204. Such instructions may be read into the main memory 204 from another computer readable medium, such as a hard disk 207 or a removable media drive 208. One or more processors 203 in a multi-processing arrangement may also be employed to execute the sequences of instructions contained in main memory 204. In alternative embodiments, hard-wired circuitry may be used in place of or in combination with software instructions. Thus, embodiments are not limited to any specific combination of hardware circuitry and software.

As stated above, the animal monitoring device 100 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, or any other non-transitory medium from which a computer can read.

Processing instructions according to the present disclosure may be stored on any one or on a combination of non-transitory computer readable media, whereby the instructions may correspond to software for controlling the animal monitoring device 100, for driving a device or devices for implementing the present disclosure, and for enabling the animal monitoring device 100 to interact with a human user (e.g., print production personnel). Such software may include, but is not limited to, device drivers, operating systems, development tools, and applications software. Such non-transitory computer readable media further includes the computer program product of the present disclosure for performing all or a portion (if processing is distributed) of the processing performed in implementing the present disclosure.

The computer code devices of the present disclosure may be any interpretable or executable code mechanism, including but not limited to scripts, interpretable programs, dynamic link libraries (DLLs), Java classes, and complete executable programs. Moreover, parts of the processing of the present disclosure may be distributed for better performance, reliability, and/or cost.

The term "computer readable medium" as used herein refers to any non-transitory medium that participates in providing instructions to the processor 203 for execution. In some examples, the computer readable storage medium may be a non-transitory computer readable medium or machine readable storage medium, such as but not limited to an optical, magnetic or semiconductor storage medium. In any case, the storage medium may store various types of computer executable instructions, such as instructions to the operations described herein. Non-limiting examples of suitable computer readable storage media that may be used include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like.

Various forms of computer readable media may be involved in carrying out one or more sequences of one or more instructions to processor 203 for execution. For example, the instructions may initially be carried on a magnetic disk of a remote computer. The remote computer can load the instructions for implementing all or a portion of the present disclosure remotely into a dynamic memory and send the instructions wirelessly and/or over one or more wired connections (e.g., a wired line using a modem). For example, a modem local to the monitoring device 100 may receive the data on the wired line and use an infrared transmitter to convert the data to an infrared signal. An infrared detector coupled to the bus 202 can receive the data carried in the infrared signal and place the data on the bus 202. The bus 202 carries the data to the main memory 204, from which the processor 203 retrieves and executes the instructions. The instructions received by the main memory 1204 may optionally be stored on storage device 207 or 208 either before or after execution by processor 203.

The monitoring device 100 contains a number monitoring sensors such as a heart rate monitor/sensor and blood pressure monitor/sensor 213, a hydration monitor/sensor and/or fatigue monitor/sensor 214, a diet/fat monitor/sensor and/or breathing monitor/sensor 215, and a wind monitor/sensor and/or weather monitor/sensor 216. A communication interface 217 is coupled to the bus 202 and provides a two-way data communication coupling to a network link 218 that is connected to, for example, a local area network (LAN) 219, or to another communications network 220 such as the Internet. For example, the communication interface 217 may be a network interface card to attach to any packet switched LAN. As another example, the communication interface 217 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 217 sends and receives electrical, electromagnetic or optical signals that carry digital data streams representing various types of information.

The network link 218 typically provides data communication through one or more networks to other data devices. For example, the network link 218 may provide a connection to another computer through a local network 219 (e.g., a LAN) or through equipment operated by a service provider, which provides communication services through a communications network 220. The local network 217 and the communications network 220 use, for example, electrical, electromagnetic, or optical signals that carry digital data streams, and the associated physical layer (e.g., CAT 5 cable, coaxial cable, optical fiber, etc.). The signals through the various networks and the signals on the network link 218 and through the communication interface 217, which carry the digital data to and from the monitoring device 100, may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The animal monitoring device 100 can transmit and receive data, including program code, through the network(s) 219 and 220, the network link 218 and the communication interface 217. Moreover, the network link 218 may provide a connection through a LAN 219 to a mobile device 221 such as a personal digital assistant (PDA) laptop computer, or cellular telephone. Also integrated in the system is a global positioning system (GPS) 222 that communicates in real time the location and position of the device, this component is integrated into the communication interface system and enables a connection with communication networks 220 and other technologies. The monitoring device 100 may optionally include a camera connection 223 that enables live video transmission to be sent through the bus 202 to the communication interface 217 to another device (e.g., device 221) used by the trainer or general user. An integrated loud speaker 224 can also be used to send auditory messages to the animal either generated autonomously by the monitoring device 100 itself or by live feed through the communication interface 217.

Figure 3:
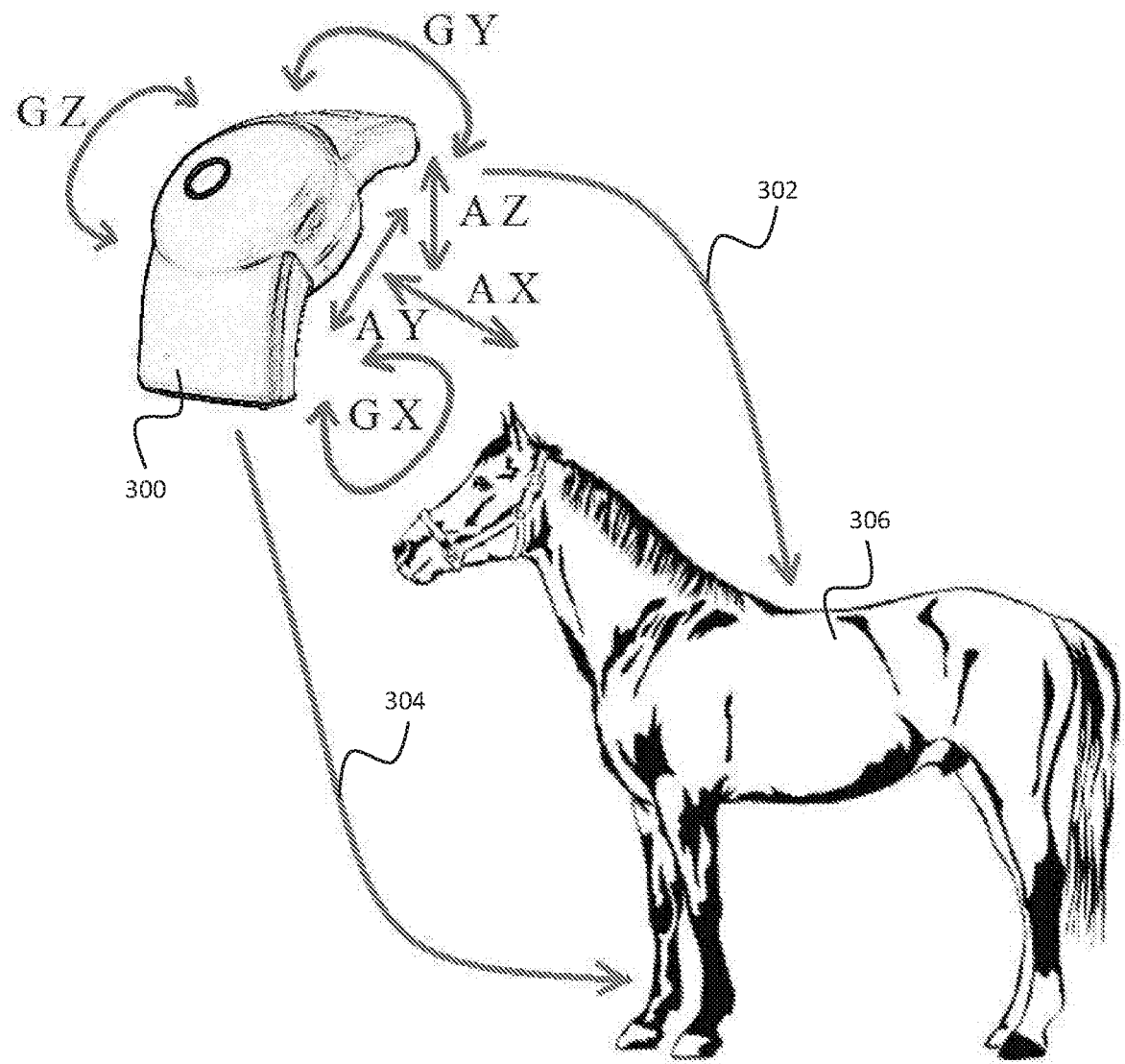
FIG. 3 is an exemplary illustration of a monitoring tag that incorporates an accelerometer, gyroscope, compass, GPS and heart monitor, it also illustrates the locations it can be placed on a horse.

One embodiment of the animal monitoring apparatus 100 includes an electronic tag 300, FIG. 3, that is small in size and light weight. Arrows 302 and 304 in FIG. 3 demonstrate two possible locations the electronic tag 300 can be placed on a horse 306, though it should be appreciated that these locations are for exemplary purposes only. The electronic tag 300 is also not limited to use on a horse and can also be used on other animals such as dogs, camels, etc. The electronic tag 300 can be placed in a number of positions such as the animals back or on the foot or ankle.

Intergrated in the electronic tag 300 are one or more accelerometers, gyroscopes, compasses, GPSs, and heartbeat monitors. The combination of the monitors will form an ability to monitor X, Y, Z, twist, acceleration and direction movements of the animal. Arrows in FIG. 3 demonstrate the movement sensors of the electronic tag 300, A X, A Y and A Z demonstrate the accelerometer monitoring movements of the electronic tag 300, G X, G Y and G Z demonstrate the monitoring Gyroscope movements. The information is matched with animal's heart rate and other physical body monitors.

Figure 4:
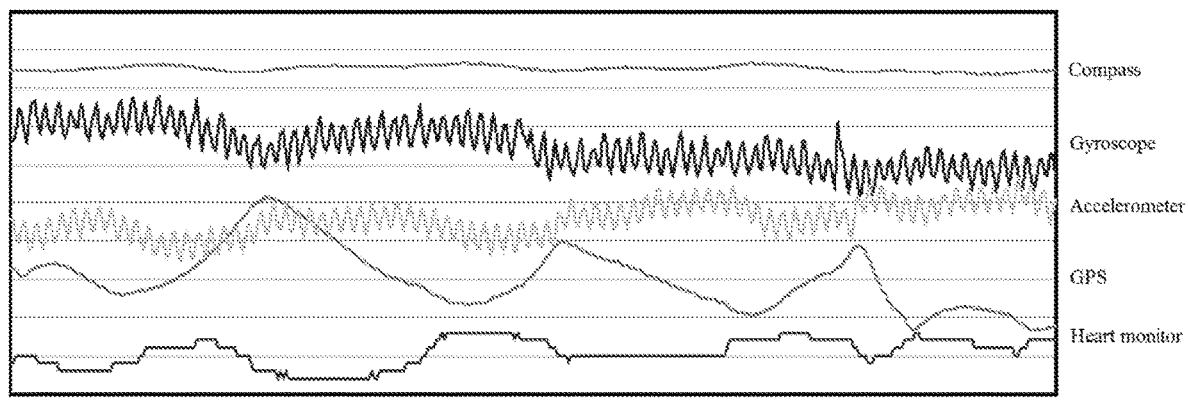
FIG. 4 illustrates exemplary readings collected from a monitoring tag.

The electronic tag 300 monitors the accelerometer (e.g., a three axis accelerometer) as well as the gyroscope and the compass. As the animal runs (for example with the electronic tag 300 on the back 302 of a horse 302), the tag 300 will collect the X, Y, Z twist, acceleration and direction movements of the animal. From the monitored movements, the animal will form a repeating action signature, an example of this is illustrated in FIG. 4. The signature incorporates all or some of the information collected from the various monitors and summerizes it mathematically to provide an evaluation of the physical well being and if it is performing as required.

The system collects information from many animals and compiles it into a database to generate a signature corresponding to the animal. The information is arranged into categories based on the type of animal, the activity it is performing, how well it is performing, etc. The system will calculate an optimum, exemplary, and/or historical signature for an animal based on it's age, weight, size and health. The system may be configured to compare a current signature of a specific animal with the optimum, exemplary, or historical signature to tell how far an animal is off it's performance expectation. In addition to the system identifying how far off the animal's performance is from it's calculated expected, optimum, exemplary, or historical performance signature, the system is setup to identify the cause of the animal's performance short comings.

Incorporated into the database, is generated list of movement signatures for horse, camel and race dog gaits. Gaits are the various ways in which an animal can move, either naturally or as a result of specialized training by humans Different gait patterns are illustrated in FIG. 5 which shows the foot steps of the different animal steps. For example, FIG. 5(a) is Walk, FIG. 5(b) is the Trot, FIG. 5(c) is the Canter and FIG. 5(d) is Gallop. In the case of horses, most breed posses these four gaits; however, some breeds do have a $5^{th}$, $6^{th}$ or $7^{th}$ that is either natural or trained.

In the case of Walk FIG. 5(a), it is a natural 4-beat movement. The horse always has two or three hooves on the ground. The walk is the slowest natural gait, it is the steadiest and most comfortable. The trot FIG. 5(b) is a steady 2-beat movement. This gait has a period of suspension. The horse springs from one diagonal to the other. In between the springs, all four legs are off the ground. The Canter FIG. 5(c) is a 3-beat movement. This has a period of suspension after each stride. This gait starts with the hind leg then leads to the front in a rocking motion. When you canter, you keep your seat in the saddle (unlike the trot). Before learning to canter, riders need to make sure they balance and their rhythm stays consistent with the horse during the trot. The gallop FIG. 5(d) is a 4-beat movement. This is similar to the canter, but the horse's legs move one at a time. The gallop feels just like a fast canter. When riding the gallop, the rider should raise their seat slightly out of the saddle, putting their weight on their heels.

With using the data collected from the electronic tag 300, the animal's gait steps can be assessed to detect if the animal is injured or needs extra coaching or training. The system can generate a report outlining the step movements, this will be assessed by a comparison program to see which foot or feet are out of step with gait steps. An extra assessment can be made to determine the possible causes of the discoordination of the steps so that the animal trainer can tend to the needs of the animal to improve its performance.

Figure 6:
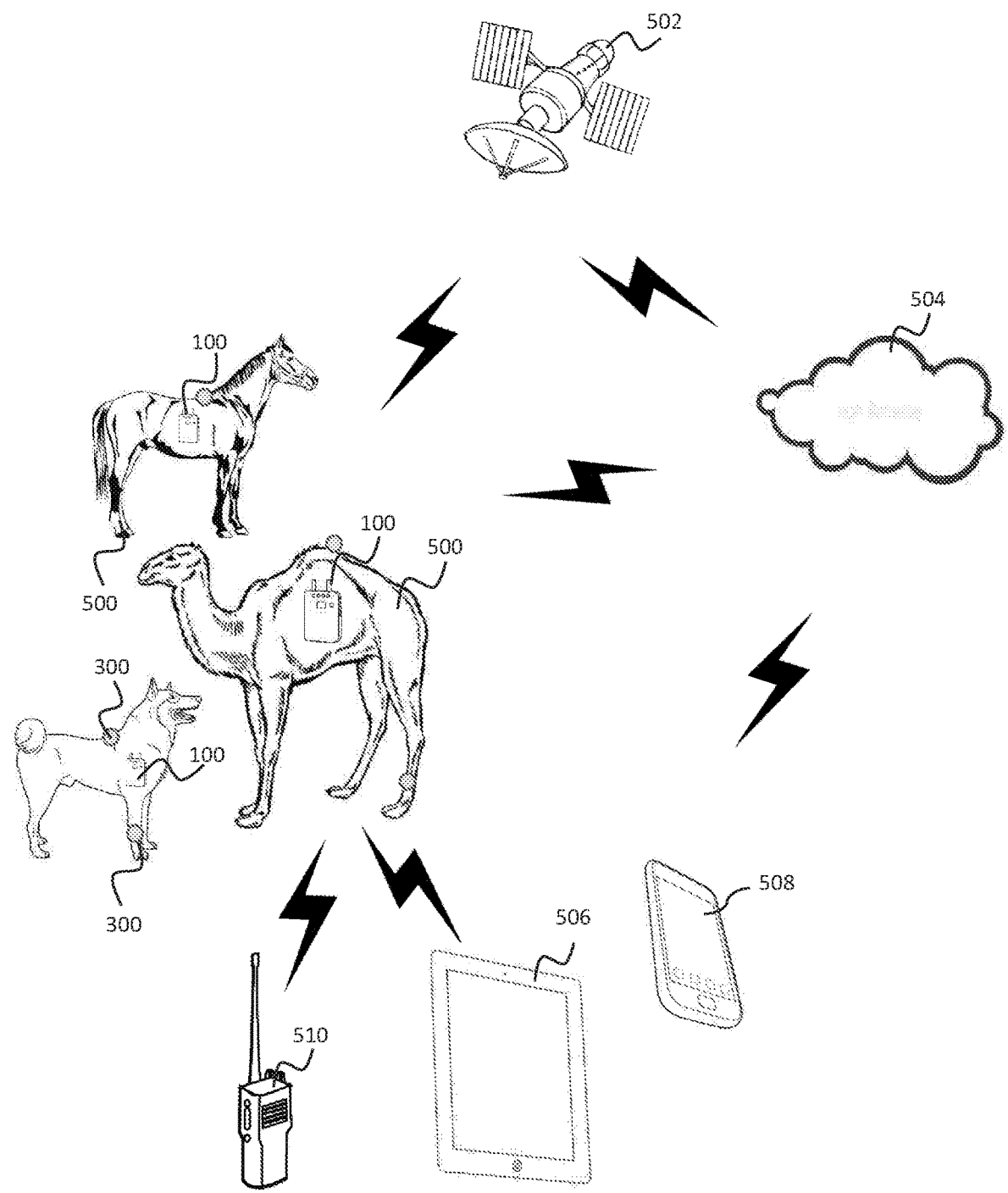
FIG. 6 map diagram of the different components associated in the system and the way they communicate with each other.

FIG. 6 is an exemplary illustration of the different connection avenues the monitoring device 100 can communicate through. While the monitoring device 100 is attached to the animal 300, it can be applied to a number of animals either domesticated racing animals 500 or animals in the wild. The animal monitoring device 100 is able to communicate through wireless Personal, Local and Wide Area Network (PAN, LAN & WAN) connectivity to a number of applications, one of which is a satellite system 502 to convey GPS coordinates for location monitoring and can also aid in tracking speed of the animal and GSM data. Data can be sent wirelessly to an on demand shared storage otherwise known the cloud 504, multiple types of data extracted from the animal with the monitoring device 100, it can be sent and stored in the cloud 504. Relevant data can then be extracted and viewed on various computing devices 506, such as lap tops, tables, personal mobile devices such as smartphones, etc. The monitoring device 100 has the ability to transfer data directly to a computing device such as a portable touch screen tablet 506 or a mobile device 508 through close range wireless data transfer, the computing devices 506 & 508 may require an additional wireless antenna to send or receive the information at a longer range to and from the monitoring device 100. In addition to the direct connection, the monitoring device 100 has the ability to receive radio signals directly from a radio transmitting device such as a walkie talkie 510. This enables the trainer or owner to send vocal signals or sounds to the animal to perhaps encourage it to run faster or to call it or calm the animal down etc. The sound will be voiced through a loud speaker 120 on the device 100 or on a secondary sound generating device connecting through one of its multiple connecting ports.

Figure 7:
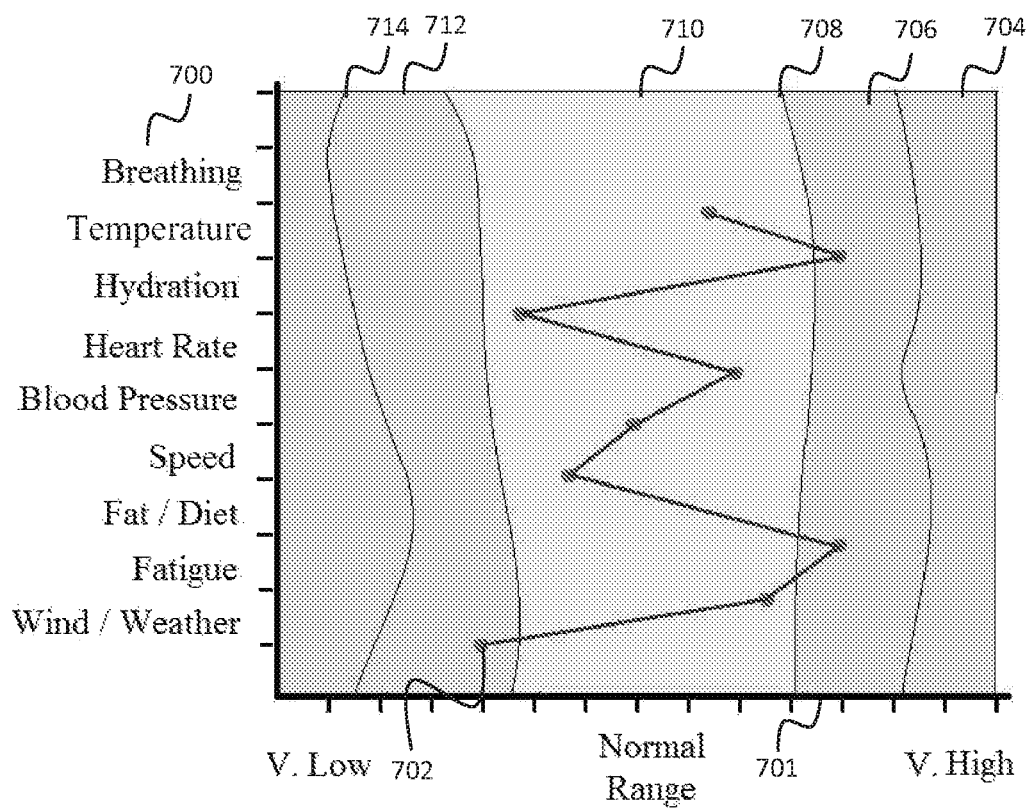
FIG. 7 shows an exemplary comparison data chart whereby data gathered from an individual animal is measured against a data set to determine its level of fitness and performance.

FIG. 7 illustrates an exemplary comparison data chart whereby data gathered from an individual animal by a monitoring device 100 is measured against a data set to determine its level of fitness and performance. The chart is designed to recognize a 'grade' level for the animal. The 'grade' refers to a categorization whereby the higher the quality the animal is the higher the grade it is categorized as. The 'grade' encompasses numerous attributes of the animal and compares it to a database of records, the animals gathered data is set against an algorithm generated from previous records. Accumulating the various data from the animal enables the system to recognize its strengths and weaknesses by matching it against a data patterns accumulated from a range of sources. The data may be stored and accessed through the cloud by multiple devices and by calculating applications for animal health and performance. By setting the data against an algorithm, the system is able to set standards of fitness and performance and grade animals accordingly.

Within the comparison data chart FIG. 7, an exemplary data range is shown in different shades. The chart logs the types of information 700 against various levels 701. The data 702 gathered from the monitoring apparatus 100 is logged into the system as the 'type' 700 and the 'level' 701. The data 702 gathered is categorized in a plurality of sectioned ranges including, but not limited to, Normal 710, High 706, Very high 704, Low 712 and Very Low 714. An example of monitoring an animal includes monitoring hydration. If the data reading falls in the Normal 710 set data range, then the data may simply be recorded and displayed for the user. However, if a reading falls in the category range of Low 712, then the system may be set to trigger a notification to the user, trainer or owner. If the data reading records and registers a reading that falls in the category range of Very Low 714, then a more immediate response can be set, for example to alert emergency services or a vet or specialist depending on the setting arranged by the user. The same application concepts can be applied to the High 706 and Very High 704 ranges as well as other monitored parameters.

Information forms a pattern and algorithm in the system, the center range 710 is illustrated in this example as the Normal range 410 indicating that monitoring results that fall in this range are the expected amount of an animal as opposed to the outer ranges 706, 704, 712, 714. The system obtains as much data as possible, examples are listed in the graph chart. The data readings formulate a pattern from scattered data results 702, these data patterns help determine the 'quality' level of the animal and categorize it into a level category that can be utilized by various users and extension applications.

Readings retrieved from animals are accumulated into a mass data base whereby the average mean, median and modes for the ranges and category levels can be adjusted to maintain accuracy. The algorithmic category allocation application will draw upon specially formed calculation formulas to accurately rate an animal on its gathered data.

Figure 8:
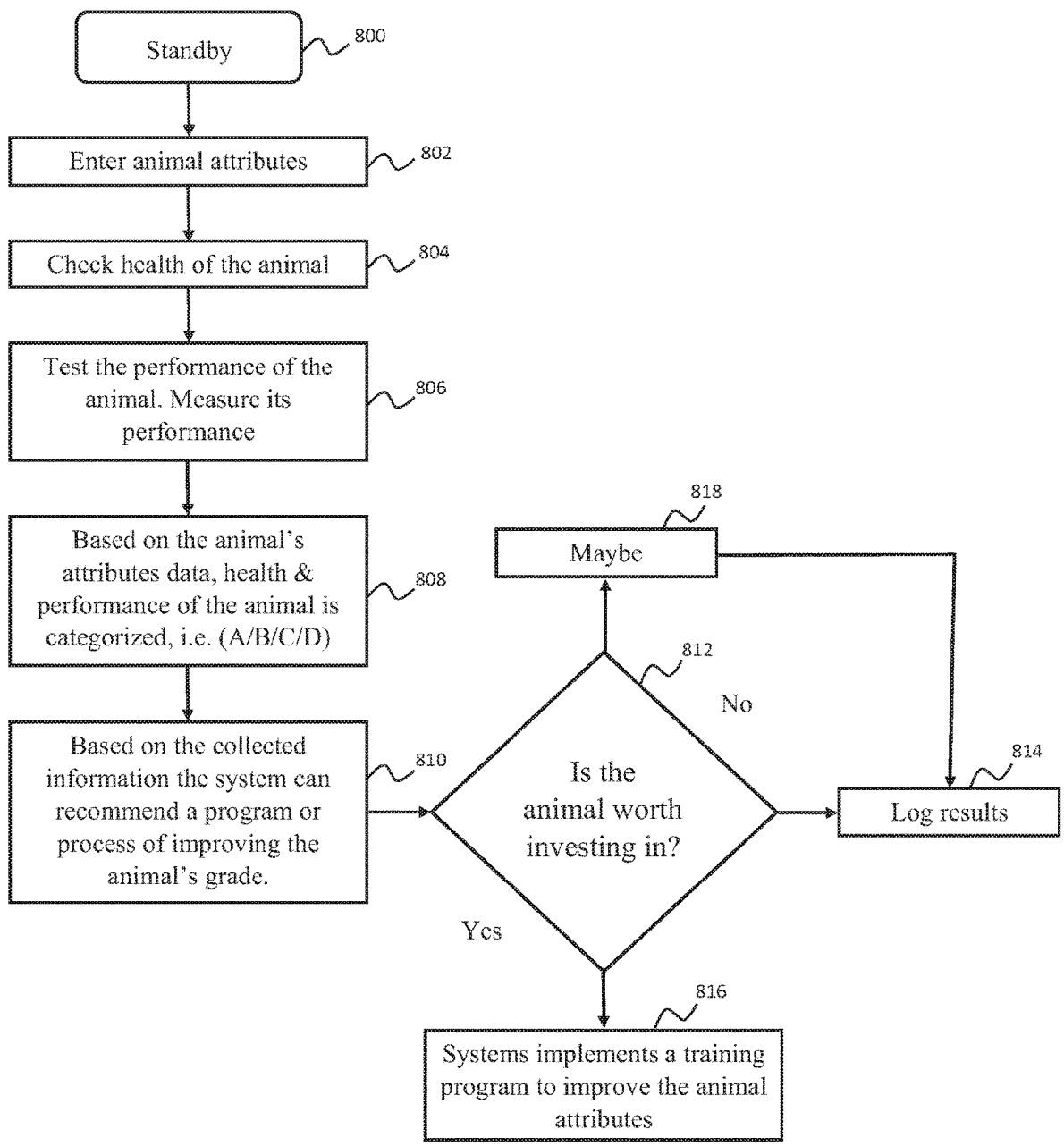
FIG. 8 is an exemplary flow diagram the user performs when using the system to automate a strategy to aid the development of an animal.

FIG. 8 details a process for an advisory system for the user to develop a strategy for aiding the owner or trainer of the animal to develop its fitness and racing speed level. The process starts with the system being in a standby 'waiting' state whereby it is ready to function on request. Within the application, the user has the ability to enter the attributes of the animal 802. Such attributes may include height, weight, age, etc. The user may also enter health attributes of the animal into the system. This may be accomplished, for example, in the form of a digital survey whereby the user is guided by the system to fill out fields within the system. In addition, the user may be able to enter information relating to any previous injuries of the animal. To simplify the calculations of the application, the user may have the option to select a condition from a condition set listed in the application. Health attributes of the animal have a contributing factor on the animal's condition and evaluation when the system determines the animal's grade.

Step 804 may include checking the health of the animal. Step 806 is a performance test of the animal, the animal monitoring device 100 tracks the animals attributes as the animal is made to run. The monitoring device 100 is attached to the animal and collects data as detailed in FIG. 7. After collecting all the various data, the system runs a calculation process set by the data ranges to evaluate a category for the quality rating it generates, step 808. The program will determine the animal's weak points and strong points to determine and recommend a process for the user or trainer to improve the animal's health and performance, this may include for example excise routine, diet, hydration improvement, etc., step 810.

A subsequent step after the calculation process can be to query the user if they wish to proceed and invest in the animal, step 812. If the user does wish to proceed with a program to advance the animal's health and performance (step 816), then they may select a 'yes' option and the system will proceed to implement an improvement program drawn from the data collected. The program will be generated from and calculated using the algorithm set to provide a guide for the user to implement over a period of time to improve its performance and grade level which in turn will improve the animal's value. Should the user select the 'No' option indicating that the user does not want to proceed with a program and invest in the animal (step 814), the system will log the results and save them in the database enabling the information to be referenced at a later date.

Results may return inconclusive after step 810 meaning the system may not be able to calculate or conclude an accurate grade rating for the animal because for example there is too much incomplete information or the user cannot decide whether they wish to invest or not. In such a scenario (step 818), the user could be offered the option of 'Maybe' and the information will be logged in the data base and if the user so wishes to retrieve it at a later date to for example complete missing required data or to simply determine whether it is a yes or no decision for that particular animal.

Figure 9:
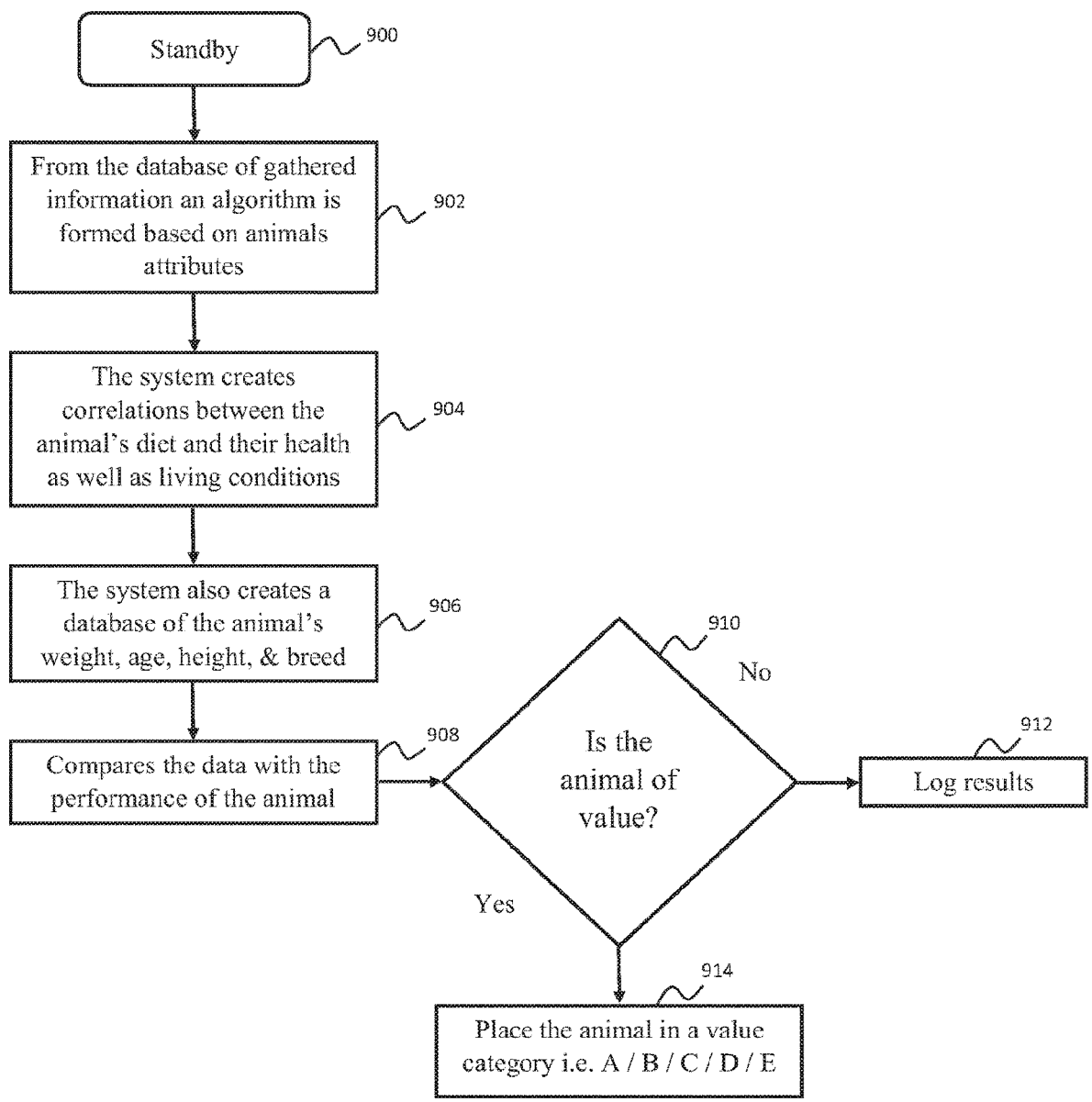
FIG. 9 is an exemplary flow diagram the system performs to obtain information of an animal, learn about its behavior and categorize its performance level.

FIG. 9 represents a process diagram for a self-learning system that over a period of time learns how to recognize a potential high value animal. The system gathers as much data as possible over a period of time and improves its accuracy as a determination process for recognizing a potential high investment potential animal. The process can include the animals breed and family history as a prominent determining factor in the process. Therefore included in the data base is a formulated animal history whereby an estimated grading is formulated on every animal listed in the family line or "family tree." When an animal is examined, a contributing factor to its grading calculation will be drawn from the animal's historic family background if it is available. An algorithmic calculation pattern can form from the collected data and be used as a contributing factor to the calculation of 'level' grade of the animal.

An exemplary process to determine an animal's value or level grade is described herein. For example, the system activates from a 'standby' state 900 and forms a calculation procedure or algorithm based on the database of animal data (step 902, for example, collected by monitoring device 100. Additionally, information relating to the health, diet and living conditions of the animal may also be used in the process of determining the health and fitness of the animal and to aid the process of understanding and calculating the grade of the animal, step 904. Each of the health, diet and living conditions may have sub processes to help determine step 904's evaluation. In addition to using information inserted from steps 902 and 904, the attributes of the animal's physical status is also included such as its weight, height, age and bread, step 906.

All or a portion of the data drawn from the animals attributes and health and living conditions are measured against the animal's performance ability, step 908. The system accumulates the data and processes it to form a value ranking to determine if the animal is of value, step 910. The ranking can also be determined by a set of optional requirements that the user enters. For example, a user may want a race dog that is "young" and is a "good breed," and the user may my not care about its fitness or diet levels as the user may be willing to improve on these aspects themselves. Alternatively, another user may disregard the importance of the animals breed but would see more value in an animal with "less weight," "good height" and "good health" perhaps for more immediate racing. After the system evaluates the inspected animal at step 908, a decision is performed on whether the animal is of value or not, step 910. For example, if the animal is of value, the animal may be categorized into a grade A/B/C etc., step 914. If the animal is not of value, then the results are logged into the data base, step 912.

Figure 10:
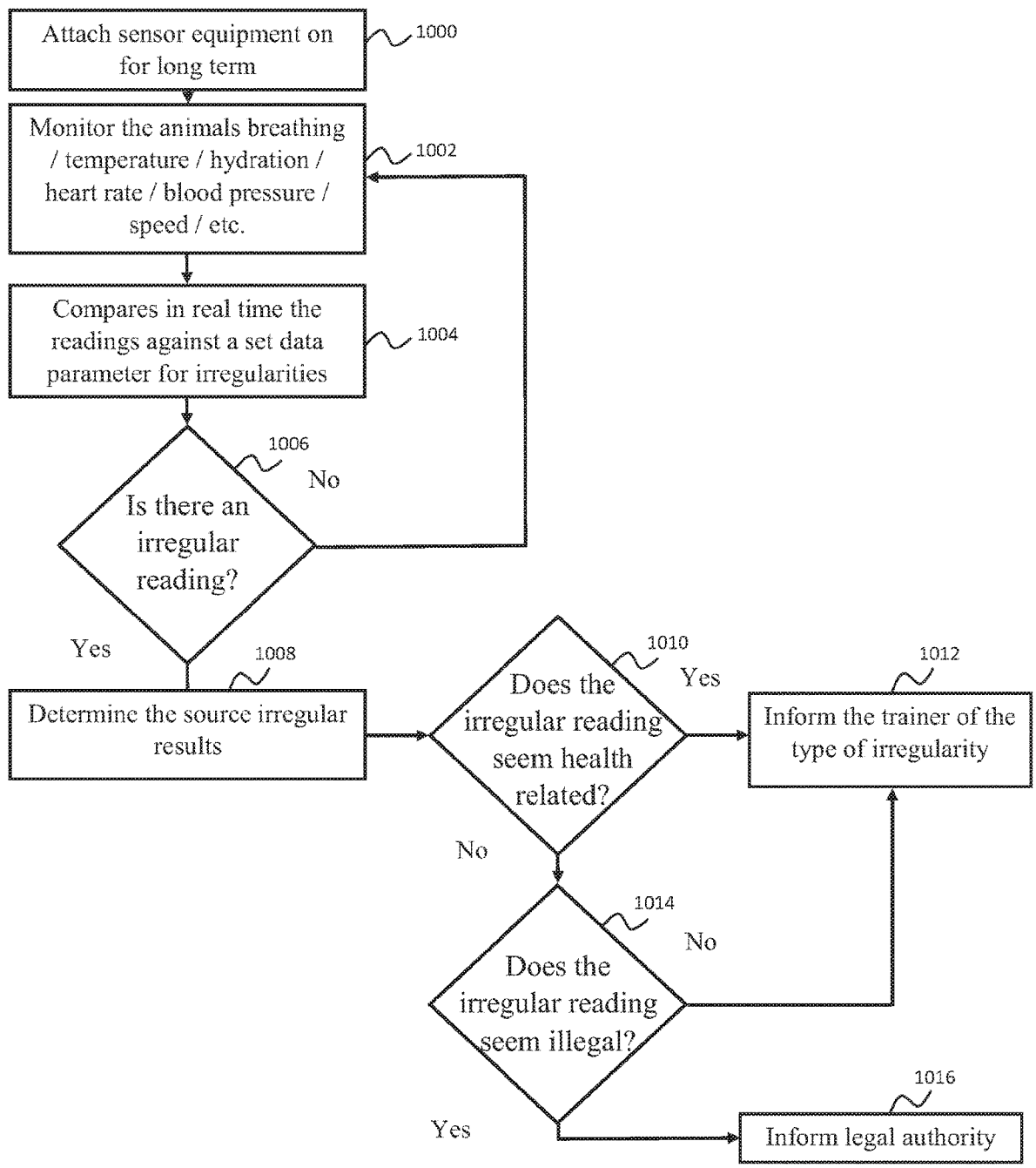
FIG. 10 is an exemplary flow diagram illustrating a method in which the attributes of an animal is monitored and set against set records to verify the animal is performing at normal levels.

FIG. 10 illustrates one embodiment of a process to determine irregularities within the performance and health of the animal. The irregularities may be related to unusual or unexpected health problems that might be caused by a health condition whether sudden or caused over a period of time. Using the readings generated by the monitoring device/system 100 described herein, irregularities indicating drug use or doping can be detected. The process can introduce a two stage procedure whereby the first stage detects an irregularity and the second stage is to determine which authority should be contacted based on the irregularity. The process detailed in FIG. 10 begins with a monitoring system 100 being attached to an animal. In at least one embodiment, the monitoring system 100 is attached to the animal and collects data over a long period of time, step 1000. The monitor device 100 tracks/records the animals' movements and its physical condition, e.g., the heart rate, temperature, hydration, blood pressure, speed, etc., step 1002. This data may be compared, e.g., in real time to the exemplary data range levels, step 1004, for example as described and illustrated in FIG. 7. As data is tracked, the readings are monitored to determine if there is an irregular reading/parameter, step 1006. If the data falls within a "normal" data range 710, then no irregularity is detected and the monitoring system 100 continues as in step 1002.

However, if an irregular reading/parameter is detected (e.g., one or more data values is outside of the "normal" range 710), then the system will attempt to determine the source of the irregular result, step 1008. In one embodiment, the system may determine whether the source of the irregular result is a health related issue or not, step 1010. The system may compare the current data values (and/or a predetermine number or time period of recent data values) obtained by the monitoring device 100 with the optimum, exemplary, or historical signature generated for the animal and/or with a current signature (which may be specific to the animal in question or may be based on aggregate data for similar animals).

The system may determine whether the irregular result is a health related issue be determining that the source of the irregular reading/parameter is due to environmental conditions, is a result of improper treatment, and/or excessive exercise of the animal. By way of an example, the system may determine if the irregular reading/parameter is due to environmental conditions (e.g., excessively cold or hot environmental temperatures), is a result of improper treatment (e.g., not enough blankets on the animal), and/or excessive exercise of the animal by comparing the activity levels of the animal (e.g., based on GPS data) and/or environmental data (e.g., wind, environmental temperature, rain/snow, etc.) with data related to the breathing, temperature, hydration, heart rate, blood pressure, or the like of the animal and/or any other data entered into the system (e.g., but not limited to, number/types of blankets/clothing on the animal, feeding schedule and amount of food, amount of water consumed, etc.).

The system may determine whether the irregular result is a health related issue based on whether the animal has consumed a sufficient amount of food or water and/or has been given proper clothing, etc. The system may also view the gait information obtained by the monitoring system 100 to determine if the animal's gate has changed, for example, due to an injury to the animal. For example, if data collected by the monitoring system 100 indicates that the speed of the animal is lower and the gait of the animal has changed, then the system may determine that the animal has a health related issue (e.g., broken or sprained leg, injured back, etc.) If the system determines that the issue is a health related one, then the person responsible for the animal will be notified with a brief what the system has detected, step 1012. The brief may identify that there is a health concern, and optionally may identify the type of health concern and/or provide potential remedies for the identified health concern. The brief may be transmitted to the user, for example, by way of an email and/or text message.

If, however, the irregularity does not seem to be health related, a second evaluation will be performed to determine if the irregular reading/parameter is from illegal activity, step 1014. Examples of illegal activity include, for example, performance enhancement drug induced doping or electro shock stimulation to increase the performance of the animal. In one embodiment, the system may determine that the irregular reading/parameter obtained by the monitoring system 100 is from illegal activity based on a comparison of the current data values (and/or a predetermined number or time period of recent data values) obtained by the monitoring device 100 with the optimum, exemplary, and/or historical signature generated for the animal and/or with the current signature (e.g., which may be specific to the animal in question). The current signature may include data values based on a recent time period (e.g., the most recent three days, the most recent week, the most recent month, etc.). As such, the current signature may differ from the optimum, exemplary, and/or historical signature (which may be based on a much longer range of time and/or on a standard animal).

For example, the system may determine that the irregular reading/parameter obtained by the monitoring system 100 is from illegal activity (e.g., performance enhancement drug induced doping) if the data obtained by the monitoring system 100 indicates that the top speed of the animal is higher than expected. For example, while the speed of the animal may increase with proper training, the amount of the increase should fall within an expected range. If the increase in speed is greater than the expected range, than the system may determine that the irregular reading/parameter is due to performance enhancement drug induced doping. In one embodiment, the speed of the animal may also be compared to at least one of the breathing, heart rate, and/or blood pressure. For example, the monitoring system 100 may determine that the irregular reading/parameter is from illegal activity if the speed of the animal is higher than expected and the breathing, heart rate, and/or blood pressure are the same or lower than expected and/or is erratic (e.g., while exercising and/or resting). As noted above, the expected values may be based on the optimum, exemplary, and/or historical signature and/or with the current signature generated for the animal.

Alternatively (or in addition), the system may determine that the irregular reading/parameter obtained by the monitoring system 100 is from illegal activity (e.g., electro shock stimulation) based on electrical signatures generated by the monitoring device 100 (e.g., using the heart rate & blood pressure monitor/sensor 213). In one example, the system may determine that the irregular reading/parameter obtained by the monitoring system 100 is from illegal activity if the electrical signatures obtained by the monitoring system 100 suddenly and/or unexpectedly increase and/or become erratic. The electrical signatures may also be compared with the speed of the animal, e.g., the monitoring system 100 may detect an illegal activity if the electrical signatures obtained by the monitoring system 100 suddenly and/or unexpectedly increase and/or becomes erratic and the speed of the animal (e.g., but not limited to the top speed) also correspondingly increases compared to the optimum, exemplary, and/or historical signature and/or with the current signature generated for the animal. Alternatively (or in addition), the detected electrical signatures may be compared to subsequent electrical signatures obtained by the monitoring device 100. For example, the electrical signatures obtained by the monitoring system 100 suddenly and/or unexpectedly increase and/or become erratic and then decreases within a predetermined amount of time after the increase and/or erratic behavior.

If it is determined that the collected data does fit a pattern wherein it is evident that illegal activities have taken place, then a secure message can be sent to the legal representative authority that possible unlawful activities have taken place and may need investigating, step 1016. If the readings do not appear to be illegal, then there may be something wrong with the animal that the system cannot determine its source. In case a case, a notification is sent to the trainer to try to identify the cause of the irregularity, step 1012.

Figure 11:
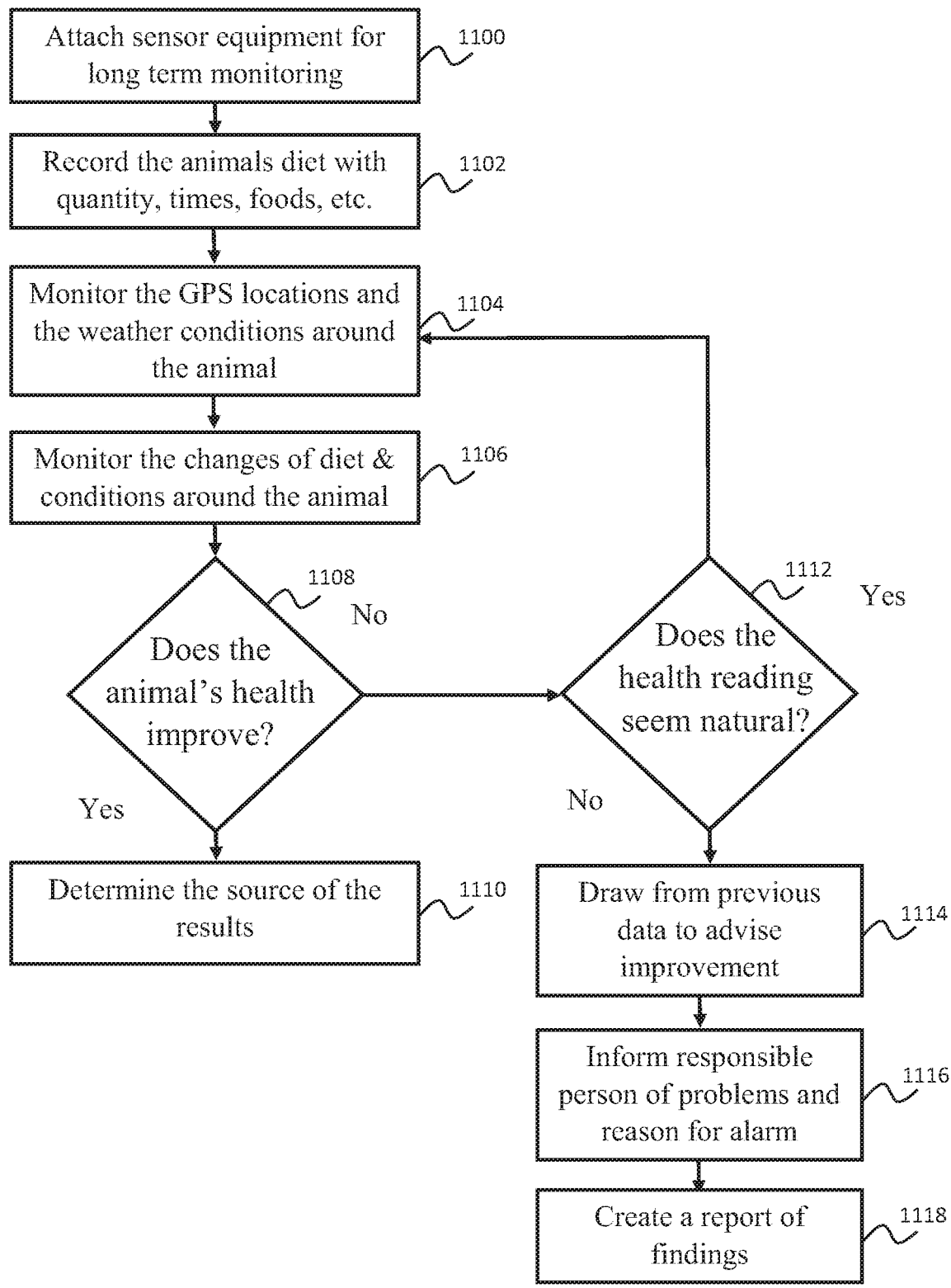
FIG. 11 is an exemplary flow diagram illustrating a method in which information is collected for heath and performance of an animal and indicates whether there is improvement or not.

FIG. 11 details a process of monitoring an animal over a long period of time using a monitoring device 100. Monitoring an animal for a long period using the monitor device 100 described herein can be useful to determine its living habitats if the animal has freedom to live in the wild or in large open areas or in a specific environment. Gathering information over a long period of time using a monitoring device 100 is applicable to many animals both in the wild or domesticated including, but not limited to, cattle, horses, camels, dogs, cats, etc. For example, researchers may find such information useful when studying animals that may be endangered or are experiencing a change of habitat due to such events as environmental global shifts in temperature or weather patterns. Collecting such a wide range of information can give the researcher valuable knowledge to help improve the animals health and environment if possible.

The process starts by attaching a physical hardware monitor 100 onto an animal and activating it, step 1100. The monitoring hardware device 100 records information on the animal and its environment, for example, the animal's diet, where the animal is sourcing its food, the quantity of food the animal is eating, the temperature of its environment, and the location of the animal, step 1102. The monitor 100 may be linked to a Global Positioning System (GPS) that pin points the location of the animal. This information links the weather condition for the location of the animal through an online real time global weather monitor, step 1104. The information is collected and recorded in a data base to be used for comparison analysis and application calculations.

The long-term monitoring system monitors the changes in diet and the conditions relating to temperature and water availability around the animal, step 1106. At certain time intervals, the system makes an assessment on whether the animal's health improves or not, step 1108. If the animal's health improves, then there may be an assessment to determine the source of the animal's improvement by either the system or the system manager 'the user," step 1110. If it is determined that the animal's health does not improve and is getting worse, then an assessment can be conducted to determine if the animal's condition deterioration is related to unnatural circumstances, step 1112. This may be determined by a user that checks the condition of the animal through the system on set periods and makes their own assessment on the animals' health, or an automated assessment can be set enabling the system to determine the nature of the change in the animals' health. If it is determined that the change is one that is natural and does not require additional analysis, then the system will return to its general monitoring state, step 1104. However, if it is concluded that the change in health condition of the animal is due to unnatural occurrences, then an advisory process will activate drawing on accumulated data and calculation algorithms to aid the user to take steps to help the animal, step 1114. In the event that emergence action is required from an emergency service or organization, the monitoring system will have the ability to alert the necessary individuals to take necessary action, step 1116. All or a portion of the information and data may be logged into the system for future reference, step 1118.

FIGS. 12A and 12B illustrate two exemplary methods to use the database of gathered information obtained by the monitoring device 100 by different market sectors. FIG. 12A generally illustrates a program that can be used on a portable wireless device. In particular, the user and/or the monitoring device 100 gather data on the animal and insert it into the application in the portable device, step 1200. It then identifies the animal's potential by comparing its data to the accessible data base of information stored on a remote server, step 1202, as described earlier in this application. The system then generates one or more improvement programs for the animal for the owner or trainer to implement, step 1204, for example, to suit the users' needs. The system then provides a list of trained practitioners in a number of animal health areas relating to the needs of the user, step 1206. The system may also link to outlets selling medicines and nutritional foods for the animal.

FIG. 12B generally illustrates a method of using data collected on an animal by the monitoring device 100 and inserting it in a platform such as a website to access by multiple users, step 1208. The website enables visitors to the site to filter through the stored information, a filtering search criteria maybe adapted to obtain results for the users preferences. The site enables users to list and sell animals, place bids to acquire a listed animal and pay for it through the platform, step 1210. The data listed in the site may be drawn from the data base of accumulated data from various sources, such as the monitoring device 100 or 300, online sources, etc.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A monitoring system for monitoring an animal, said monitoring system comprising:
   a plurality of biological sensors configured to generate a plurality of biological parameters of said animal;
   at least one location sensor configured to generate location parameters of said animal;
   at least one ambient weather sensor configured to generate weather parameters corresponding to ambient weather conditions proximate said animal;
   at least one processor; and
   one or more computer-readable non-transitory storage mediums comprising data representing at least one signature corresponding to said animal, wherein at least one of said computer-readable non-transitory storage mediums further includes instructions stored thereon which when executed by said at least one processor result in the following operations for determining the health of said animal, said operations comprising:
   comparing at least one of said parameters generated by said sensors with said data representing at least one signature corresponding to said animal to determine if there is an irregular parameter, wherein in response to an irregular parameter being identified, then:
      determining if said identified irregular parameter is related to a health condition of said animal; and
      if said identified irregular parameter is not related to said health condition of said animal, then determining if said identified irregular parameter is related to an illegal activity, wherein determining if said identified irregular parameter is related to said illegal activity comprises comparing current parameters obtained by said monitoring system with said signature corresponding to said animal.

2. The monitoring system of claim 1, wherein said plurality of biological sensors includes one or more selected from the following group consisting of a heart rate sensor, a blood pressure sensor, a hydration sensor, a fatigue sensor, a diet/fat sensor, and a breathing sensor.

3. The monitoring system of claim 1, wherein said data representing said at least one signature corresponding to said animal is based on data collected by said monitoring system.

4. The monitoring system of claim 1, wherein determining if there is an irregular parameter comprises comparing said at least one parameter generated by said sensors with said data representing said at least one signature corresponding to said animal to determine said at least one parameter generated by said sensors is outside of an expected range.

5. The monitoring system of claim 1, wherein said signature corresponding to said animal comprises a historic signature based on parameters collected by said monitoring system.

6. The monitoring system of claim 1, wherein determining if said identified irregular parameter is related to said illegal activity comprises detecting performance enhancement drug induced doping.

7. The monitoring system of claim 6, wherein determining if said identified irregular parameter is related to performance enhancement drug induced doping comprises comparing a top speed of said animal is higher than expected based on said at least one signature.

8. The monitoring system of claim 7, wherein determining if said identified irregular parameter is related to performance enhancement drug induced doping comprises determining that said top speed of said animal is higher than expected and at least one of the breathing, heart rate, and/or blood pressure are the same or lower than expected and/or is erratic.

9. The monitoring system of claim 1, wherein determining if said identified irregular parameter is related to said illegal activity comprises detecting electro shock stimulation.

10. The monitoring system of claim 9, wherein determining if said identified irregular parameter is related to electro shock stimulation is based on electrical signatures generated by the monitoring device.

11. The monitoring system of claim 10, wherein said identified irregular parameter is determined to be related to electro shock stimulation in response to said electrical signatures obtained by said monitoring system suddenly and/or unexpectedly increasing and/or becoming erratic and said speed of said animal also correspondingly increasing.

12. The monitoring system of claim 10, wherein said identified irregular parameter is determined to be related to electro shock stimulation in response to said electrical signatures suddenly and/or unexpectedly increasing and/or becoming erratic and then decreasing within a predetermined amount of time after said increase and/or said erratic behavior.

13. A method for monitoring an animal, said method comprising:
receiving a plurality of biological parameters of said animal from a plurality of biological sensors;
receiving location parameters of said animal from at least one location sensor;
receiving weather parameters corresponding to ambient weather conditions proximate said animal from at least one ambient weather sensor; and
comparing at least one of said parameters generated by said sensors with data representing at least one signature corresponding to said animal to determine if there is an irregular parameter, wherein in response to an irregular reading/parameter being identified, then:
determining if said identified irregular parameter is related to a health condition of said animal; and
if said identified irregular parameter is not related to said health condition of said animal, then determining if said identified irregular parameter is related to an illegal activity, wherein determining if said identified irregular parameter is related to said illegal activity comprises detecting performance enhancement drug induced doping.

14. The method of claim 13, wherein determining if said identified irregular parameter is related to performance enhancement drug induced doping comprises comparing a top speed of said animal is higher than expected based on said at least one signature.

15. The method of claim 14, wherein determining if said identified irregular parameter is related to performance enhancement drug induced doping comprises determining that said top speed of said animal is higher than expected and at least one of the breathing, heart rate, and/or blood pressure are the same or lower than expected and/or is erratic.

16. A for monitoring an animal, said method comprising:
receiving a plurality of biological parameters of said animal from a plurality of biological sensors;
receiving location parameters of said animal from at least one location sensor;
receiving weather parameters corresponding to ambient weather conditions proximate said animal from at least one ambient weather sensor; and
comparing at least one of said parameters generated by said sensors with data representing at least one signature corresponding to said animal to determine if there is an irregular parameter, wherein in response to an irregular reading/parameter being identified, then:
determining if said identified irregular parameter is related to a health condition of said animal; and
if said identified irregular parameter is not related to said health condition of said animal, then determining if said identified irregular parameter is related to an illegal activity, wherein determining if said identified irregular parameter is related to said illegal activity comprises detecting electro shock stimulation.

17. The method of claim 16, wherein determining if said identified irregular parameter is related to electro shock stimulation is based on electrical signatures generated by the monitoring device.

18. The method of claim 17, wherein said identified irregular parameter is determined to be related to electro shock stimulation in response to said electrical signatures obtained by said monitoring system suddenly and/or unexpectedly increasing and/or becoming erratic.

* * * * *